United States Patent
Baegert et al.

(10) Patent No.: US 12,383,346 B2
(45) Date of Patent: Aug. 12, 2025

(54) AUTOMATIC DETECTION OF TRACKING ARRAY MOTION DURING NAVIGATED SURGERY

(71) Applicant: DEPUY IRELAND UNLIMITED COMPANY, County Cork (IE)

(72) Inventors: Claire Baegert, Grenoble (FR); Adrien Anxionnat, Allemond (FR)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 147 days.

(21) Appl. No.: 18/153,855

(22) Filed: Jan. 12, 2023

(65) Prior Publication Data

US 2024/0238046 A1 Jul. 18, 2024

(51) Int. Cl.
*A61B 34/20* (2016.01)

(52) U.S. Cl.
CPC ...... *A61B 34/20* (2016.02); *A61B 2034/2055* (2016.02); *A61B 2034/2065* (2016.02)

(58) Field of Classification Search
CPC .... A61B 2034/2055; A61B 2034/2065; A61B 34/20
See application file for complete search history.

(56) References Cited

U.S. PATENT DOCUMENTS

| | | | |
|---|---|---|---|
| 7,643,862 B2 | 1/2010 | Schoenefeld | |
| 9,452,023 B2 | 9/2016 | Boillot | |
| 11,109,777 B2 | 9/2021 | Stein | |
| 11,123,253 B2 | 9/2021 | Anderson | |
| 11,141,227 B2 | 10/2021 | Shoham | |
| 11,191,594 B2 | 12/2021 | Morgan | |
| 11,224,443 B2 | 1/2022 | Amiot | |
| 11,229,520 B2 | 1/2022 | Fanson | |
| 11,298,196 B2 | 4/2022 | Crawford | |
| 2005/0109855 A1* | 5/2005 | McCombs | A61B 90/36 236/100 |
| 2007/0016009 A1* | 1/2007 | Lakin | A61B 90/39 600/424 |
| 2020/0069372 A1 | 3/2020 | Dufour | |

(Continued)

FOREIGN PATENT DOCUMENTS

| | | |
|---|---|---|
| AU | 2020201097 A1 | 9/2020 |
| EP | 3878393 A2 | 9/2021 |

(Continued)

OTHER PUBLICATIONS

Brainlab, "Knee3 Surgical Technique", pp. 1-58, 2015 (Year: 2015).*

(Continued)

*Primary Examiner* — Jeffrey G Hoekstra
*Assistant Examiner* — Nyrobi Celestine
(74) *Attorney, Agent, or Firm* — Kramer & Amado, P.C.

(57) ABSTRACT

A system and method for detecting movement of a first navigation array relative to a bone during computer-assisted surgery, including: monitoring a location of a landmark on the bone using the first navigation array, wherein the landmark is at a first end of the bone and the first navigation array is adjacent to a second end of the bone; determining that the location of the landmark has moved a distance greater than a threshold value; and indicating suspicious activity when the distance is greater than the threshold value.

16 Claims, 13 Drawing Sheets

(56) References Cited

U.S. PATENT DOCUMENTS

| | | |
|---|---|---|
| 2021/0128250 A1 | 5/2021 | Chav |
| 2021/0186711 A1 | 6/2021 | van der Walt |
| 2021/0369349 A1 | 12/2021 | Haider |
| 2022/0008136 A1 | 1/2022 | Cameron |
| 2022/0047335 A1* | 2/2022 | Morgan ................. A61B 17/88 |
| 2022/0096166 A1 | 3/2022 | Couture |
| 2022/0125517 A1 | 4/2022 | Zimmermann |

FOREIGN PATENT DOCUMENTS

| | | |
|---|---|---|
| EP | 3936075 A2 | 1/2022 |
| WO | 2020185930 A1 | 9/2020 |
| WO | 2022/238437 A1 | 11/2022 |

OTHER PUBLICATIONS

International Search Report & Written Opinion mailed on Mar. 27, 2024 for PCT/EP2024/050464.

Gary W. Doan et. al, "Image-Free Robotic-Assissted Total Knee Arthroplasty Improves Implant Alignment Accuracy: A Cadaveric Study", The Journal of Arthroplasty, 2022, pp. 795-801, vol. 37.

\* cited by examiner

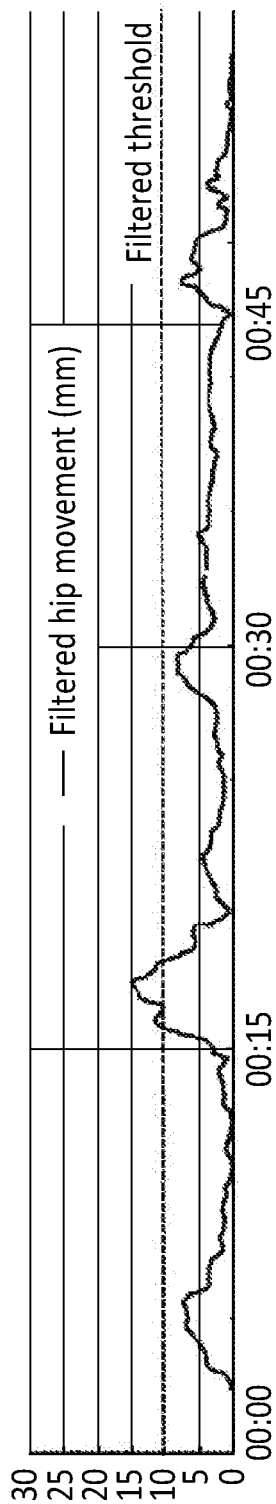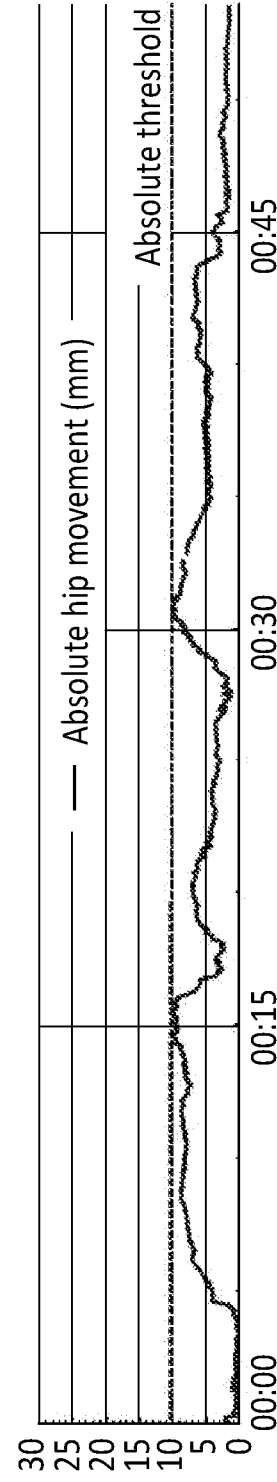
FIG. 5B
FIG. 5C

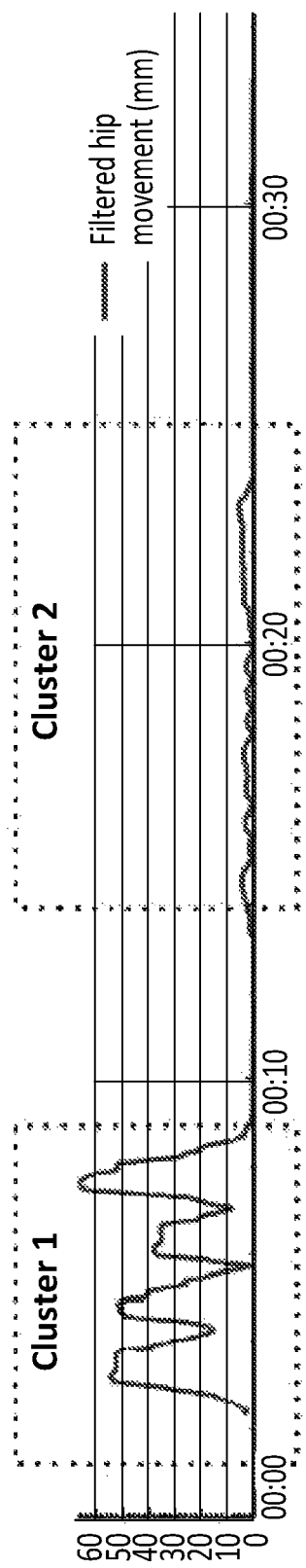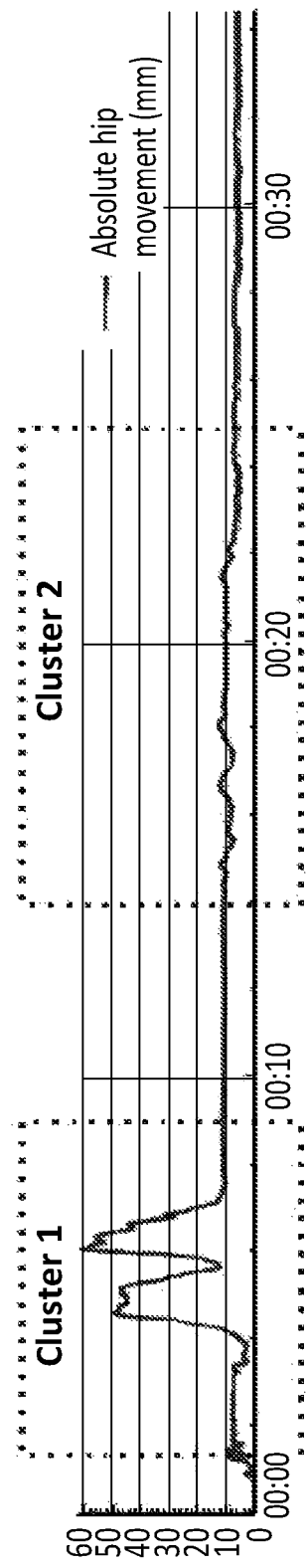

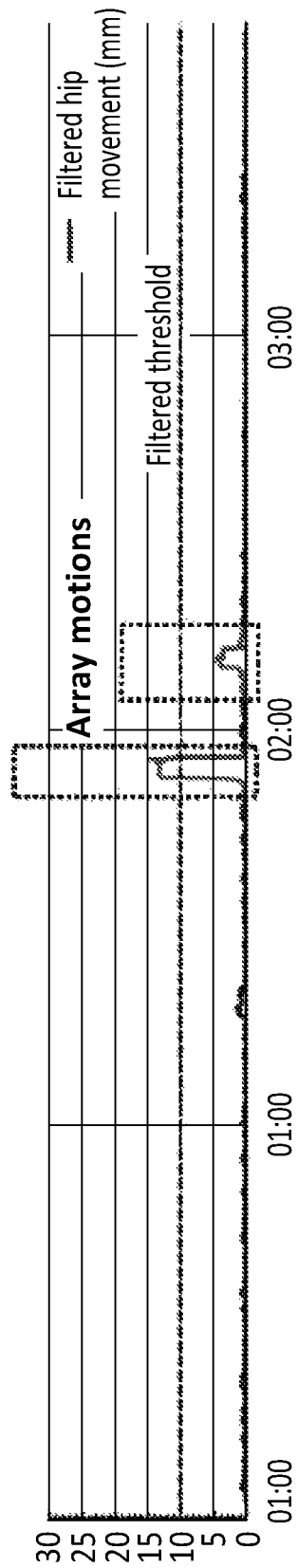
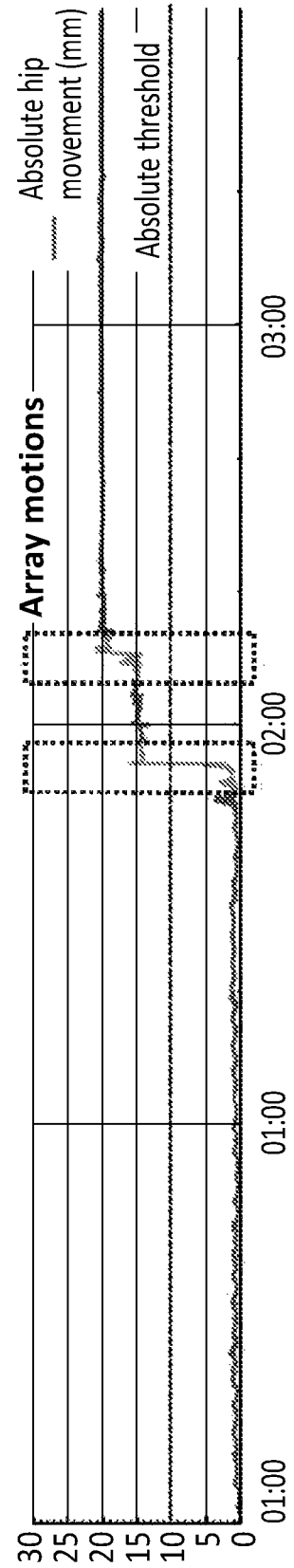
FIG. 7B
FIG. 7C

AUTOMATIC DETECTION OF TRACKING ARRAY MOTION DURING NAVIGATED SURGERY

TECHNICAL FIELD

Various exemplary embodiments disclosed herein relate to automatic detection of tracking array motion during navigated surgery based upon landmark motion analysis.

BACKGROUND

A computer-assisted surgical system may include a robot arm, controller, and navigational system. Robotic or robot-assisted surgeries have many associated advantages, particularly in terms of precise placement of surgical tools and/or implants. For example, in surgeries where multiple steps are carried out, such as, by way of a non-limiting example, a drill, tap, and screw technique, the conceptual ability of a robotic surgical system to track a position and/or orientation of a first tool to achieve a desired trajectory and then later precisely return to the same position and/or orientation with a second tool at a desired trajectory is particularly advantageous.

Whatever the principle of the computer-assisted surgical system, the position of the tools relative to the bone fully relies on navigation arrays rigidly attached on each element. Any event impacting the rigid attachment of the elements to their respective navigation array will introduce error and therefore bring down the accuracy of the system. Accordingly, there is a need for systems, devices, and methods that improve computer-assisted surgical systems, for example, by automatically detecting when tracking arrays move relative to the bone.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method of detecting movement of a first navigation array relative to a bone during computer-assisted surgery, including: monitoring a location of a landmark on the bone using the first navigation array, wherein the landmark is at a first end of the bone and the first navigation array is adjacent to a second end of the bone; determining that the location of the landmark has moved a distance greater than a threshold value; and indicating suspicious activity when the distance is greater than the threshold value.

Various embodiments are described, further including: monitoring the location of a second navigation array; analyzing a similarity of a motion of the second navigation array and the landmark; and determining that the suspicious activity is camera motion when the motion of the second navigation array and the landmark are similar.

Various embodiments are described, wherein analyzing the similarity of the motion of the second navigation array and the landmark includes: monitoring a frame-to-frame movement of the landmark and the second navigation array; and comparing the frame-to-frame movement of the landmark to the frame-to-frame movement of the second navigation array.

Various embodiments are described, further including: computing bone motion information; and analyzing landmark metrics based upon the bone motion information to determine whether bone motion information indicates that the suspicious activity is array motion.

Various embodiments are described, further including: analyzing landmark metrics based upon bone motion information to determine whether bone motion information indicates that the suspicious activity is bone motion.

Various embodiments are described, wherein the computer-assisted surgery is a knee surgery and the landmark is a hip center.

Various embodiments are described, wherein the landmark is at a location that moves less than a threshold value during the computer-assisted surgery.

Various embodiments are described, further including: monitoring the location of a second navigation array; and analyzing, using a machine learning model, a similarity of a motion of the second navigation array and the landmark and determining that the suspicious activity is camera motion when the motion of the second navigation array and the landmark are similar.

Various embodiments are described, further including: computing bone motion information; and analyzing, using a machine learning model, landmark metrics based upon the bone motion information to determine whether bone motion information indicates that the suspicious activity is array motion or is bone motion.

Further various embodiments relate to a method of detecting movement of a first navigation array relative to a femur during computer-assisted knee surgery, including: monitoring a location of a hip center of the femur using the first navigation array, wherein the first navigation array is adjacent to knee; determining that the location of the hip center has moved a distance greater than a threshold value; and indicating suspicious activity when the distance is greater than the threshold value.

Various embodiments are described, further including: monitoring the location of a second navigation array; analyzing a similarity of a motion of the second navigation array and the hip center; and determining that the suspicious activity is camera motion when the motion of the second navigation array and the hip center are similar.

Various embodiments are described, wherein analyzing the similarity of the motion of the second navigation array and the hip center includes: monitoring a frame-to-frame movement of the hip center and the second navigation array; and comparing the frame-to-frame movement of the hip center to the frame-to-frame movement of the second navigation array.

Various embodiments are described, further including: computing leg motion information; and analyzing hip center metrics based upon the leg motion information to determine whether leg motion information indicates that the suspicious activity is array motion.

Various embodiments are described, further including: analyzing hip center metrics based upon the leg motion information to determine whether leg motion information indicates that the suspicious activity is leg motion.

Various embodiments are described, further including: monitoring the location of a second navigation array; analyzing, using a machine learning model, a similarity of a motion of the second navigation array and the hip center;

and determining that the suspicious activity is camera motion when the motion of the second navigation array and the hip center are similar.

Various embodiments are described, further including: computing leg motion information; and analyzing, using a machine learning model, landmark metrics based upon the leg motion information to determine whether leg motion information indicates that the suspicious activity is array motion or is leg motion.

BRIEF DESCRIPTION OF THE DRAWINGS

In order to better understand various exemplary embodiments, reference is made to the accompanying drawings in the following listing.

FIGS. 5A-C represents plots of landmarks motion in a surgical step where the leg moves significantly.

FIGS. 6A-C represent plots of landmarks motion in a surgical step where there is both camera and leg motion events.

FIGS. 7A-C represent plots of landmarks motion in a surgical step where a navigation array moves relatively to a bone.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1:
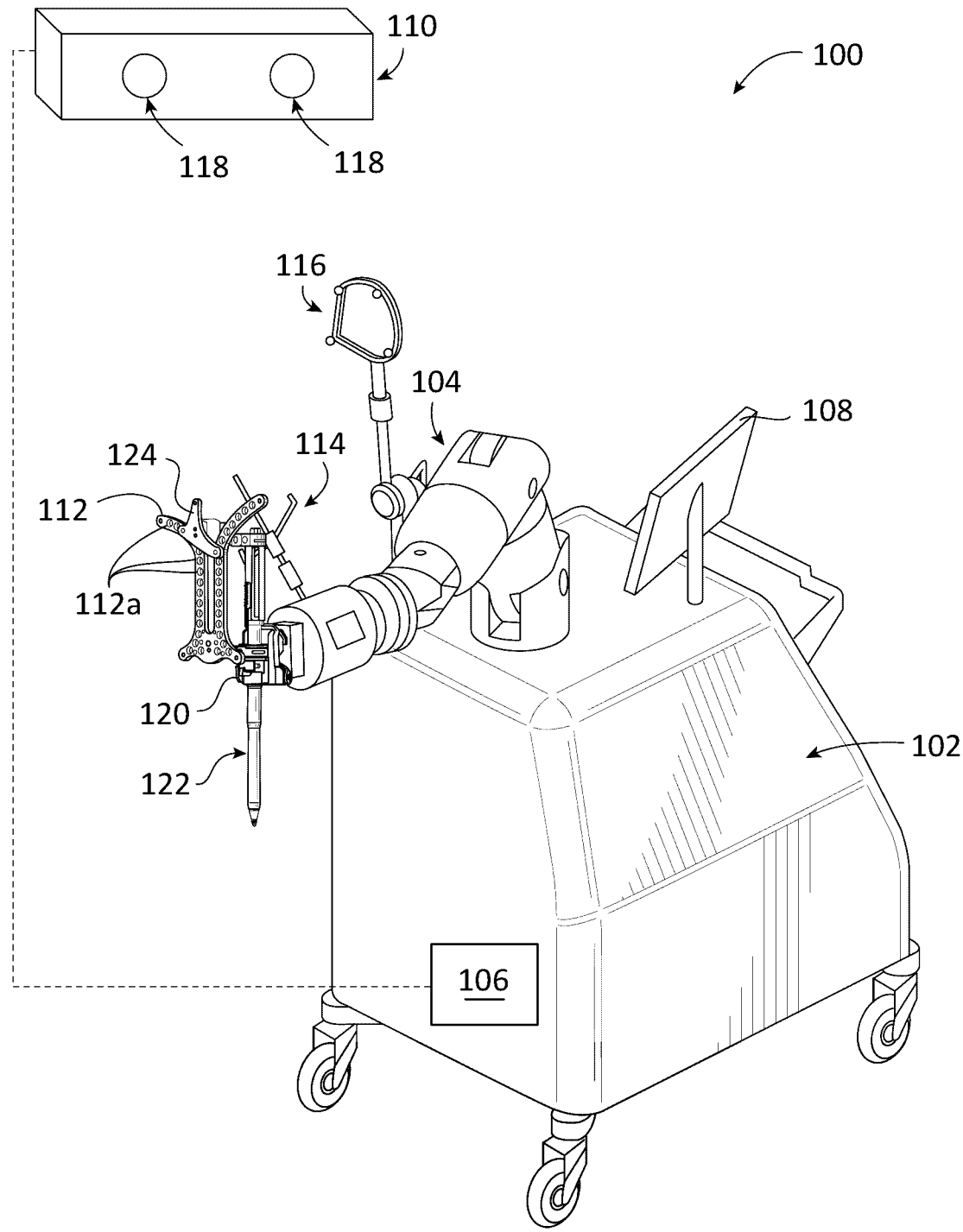
FIG. 1 illustrates an overview of a computer-assisted surgical system.

FIG. 1 illustrates an overview of a computer-assisted surgical system 100. A surgical robot base 102 supports a robot arm 104. The base 102 is depicted as a mobile base, but stationary bases are also contemplated. The robot arm 104 includes a plurality of arm segments connected by rotatable or otherwise articulating joints and may be moved by actuation of the joints, locked in place, etc. The robot arm 104 is able to move in all six degrees of freedom during a surgical procedure. The robot arm 104 may be configured for incremental changes (e.g., in each of the six degrees of freedom) to ensure the necessary precision during surgery. The robot arm 104 may actively move about the joints to position arm in a desired position relative to the patient (not depicted), or the robot arm may be set and locked into a position. For example, tools may be used by users with some degree of robotic assistance by, for example, placing a guiding tube in a precise location and orientation, and then the user uses the guiding tube to guide the tool. In other situations, a cutting tool may be attached to the robot arm 104, and the robot arm carries out a surgical step such as cutting or drilling using the attached cutting tool.

A control unit or controller 106 controls the robot arm 104 and associated navigational system(s). The controller 106 typically includes a power supply, AC/DC converters, motion controllers to power the motors of the actuation units in each joint, fuses, real-time interface circuits, and other components conventionally included in robotic surgical systems. An external device 108 may communicate with the controller 106. The external device 108 may be a display, a computing device, remote server, etc., configured to allow a surgeon or other user to input data directly into the controller 106. Such data may include patient information and/or surgical procedure information. The external device 108 may display information from the controller 106, such as alerts. Communication between the external device 108 and the controller 106 may be wireless or wired.

The system 100 may also include a navigational system that includes a tracking unit 110, such that the relative pose or three-dimensional position and orientation of fiducials attached to a plurality of the navigational system navigation arrays (e.g., a navigation array 112, a navigation array 114, and an optional navigation array 116 (and/or other navigation arrays)) may be tracked in real time and shared with the controller 106 for planning or control. The tracking unit 110 may measure the relative motions between any and all components coupled to navigation arrays in a known manner. Tracking may be performed in a number of ways, e.g., using stereoscopic optical detectors 118, ultrasonic detectors, radio frequency (RF) location detectors, sensors configured to receive position information from inertial measurement units, etc. Tracking in real time, in some embodiments, means high frequencies greater than twenty Hertz, in some embodiments in the range of one hundred to five hundred Hertz, with low latency, and in some embodiments less than five milliseconds. Regardless of how it is gathered, position and orientation data may be transferred between components (e.g., to the controller 106) via any suitable connection, e.g., with wires or wirelessly using a low latency transfer protocol. The real-time controller 106 may carry out real-time control algorithms at a reasonably high frequency with low additional latency to coordinate movement of the system 100. The tracking unit may also include cameras, or use the stereoscopic optical detectors 116, to detect, for example, characteristics of end effectors attached to the robot arm 104.

Fiducials (not depicted) of the navigational system may be attached to the navigation arrays (e.g., the navigation array 112, the navigation array 114, and/or optional navigation array 116 (and/or other navigation arrays)), for example, via a plurality of mounting points 112a (e.g., of the navigation array 112). Fiducials may be arranged in predetermined positions and orientations with respect to one another. The fiducials may be aligned to lie in planes of known orientation (e.g., perpendicular planes, etc.) to enable setting of a Cartesian reference frame. The fiducials may be positioned within a field of view of a navigation system and may be identified in images captured by the navigation system. The fiducials may be single-use reflective navigation markers. Exemplary fiducials include infrared reflectors, light emitting diodes (LEDs), radio frequency (RF) emitters, spherical reflective markers, blinking LEDs, augmented reality markers, and so forth. The navigation arrays may be or may include an inertial measurement unit (IMU), an accelerometer, a gyroscope, a magnetometer, other sensors, or combinations thereof. The sensors may transmit position and/or orientation information to a navigation system, e.g., to a processing unit of the navigation system, which may be, for example, the controller 106.

The navigation array 114 may be mounted on the robot arm 104 to determine a position of the robot arm or a distal portion thereof (indicative of an end effector position or with reference to a difference from a position of the navigation array 112). The structure and operation of the navigation array 114 may vary depending on the type of navigation system used. In some embodiments, the navigation array 114 may include one or more sphere-shaped or other fiducials for use with an optical navigation system, for example, a robotic navigation system. The navigation system may facilitate registering and tracking of the position and/or orientation of the navigation array 114 and, by extension, an end effector 120 and its relative distance to other objects in the operating room, e.g., a patient, a surgeon, etc.

The end effector 120 may be coupled to the robot arm 104, for example, via an end plate locked by a lever. As can appreciated, there should be no play between the end effector 120 and robot arm 104. While the system 100 may utilize end effectors of various shapes, sizes, and functionalities, the depicted end effector has an aperture for removably retaining a tool 122. In some embodiments, the navigation array 112 is mounted to the end effector. Advantageously, the end effector 120 may be adapted to retain a series of tools including the tool 122 (for example, a series of tools used in a particular surgical procedure).

The tool 122 may be placed in a guide (e.g., or another aperture) of the end effector 120. A locking mechanism of the end effector 120 may secure the tool 122 in place. The locking mechanism may be a slider locking mechanism or other feature. The tool 122 as depicted is a dilator, but it is understood that the tool may have at a distal end: a probe, a dilator tip (e.g., sharp or blunt), a cutting instrument, a tap, a screw, etc. The cutting instrument may be, for example, a drill, saw blade, burr, reamer, mill, scalpel blade, or any other implement that could cut bone or other tissue and is appropriate for use in a given operation. In some embodiments, the navigation array 112 may be attached to the robot.

Navigation arrays may also be attached to the patient in known locations. Typically these navigation arrays are attached to bones of the patient. Once the navigation arrays are attached to the patient's bones, X-rays or other images may be used to register the location of the arrays to the patient's bones. Because the navigation arrays may be viewed and tracked by the tracking unit 110, the tracking unit 110 can determine the relative location of the tool 122 to the patient anatomy by tracking the location of the navigation arrays attached to the patient and then the registration information of the navigation arrays to the patient's bones.

Computer-assisted surgery may be much more accurate than conventional surgery. See for example, G. W. Doan et al., Image-Free Robotic-Assisted Total Knee Arthroplasty Improves Implant Alignment Accuracy: A Cadaveric Study, The Journal of Athroplasty, Vol. 37, Issue 4, pages 795-801. This accuracy depends on the navigation arrays being securely attached to the bones of the patient without movement of the navigation array. A source of accuracy errors occurs when a navigation array attached to the bone moves relative to the bone during surgery. This shifts the reference frame used by the tracking unit 110 to determine the location of the patient relative to the tool. Currently, this potential source of error can be addressed by providing for a reproducible landmark on the bone that may be checked anytime during the surgery. This specific check can be included in the surgical workflow or the surgeon can take the initiative to do this check which adds additional steps to the surgery. However, this approach only guarantees that the array did not move at a specific point of surgery, or when a user has a doubt. In reality, it is likely that the array moved due to an event that is not known to the user, because he is focusing on something else. That can be the case during the cut for example. This potential source of error can also be addressed by connecting a single fiducial to the bone (sometimes called a surveillance marker) and having the system continually monitor the position of the fiducial relative to the surveillance marker. However, this additional surveillance marker adds time to the procedure and requires an additional cut into the bone. Accordingly, embodiments of a system that automatically detects navigation array motion relative to the patient's bones during navigated surgery based on landmarks motion analysis, and without a surveillance marker, will now be described.

In other embodiments, the computer-assisted surgery may be performed without a robot.

In the following description, the example of knee surgery will be used where navigation arrays are attached to the tibia and femur. This approach may be applied to other surgeries as well. When an array moves relative to the bone to which it is affixed ("array-bone relative movement"), the camera in the tracking system sees a change in the array position, but the position of the patient landmarks will change as well as they are derived from the array position. This relative motion viewed by the tracking unit 110 is similar to other motions that may occur in the system such as camera or patient leg motion. In order to differentiate array movement relative to the bone from these other motions, motion data may be filtered by amplitude, duration, translation, etc. in order to differentiate array-bone relative movement from other types of movement in the system. For example, camera movement is an event in a defined timeframe that impacts similarly the localization information provided by the camera for all visible arrays. Leg movements may have very different durations or amplitudes, for example: a big leg motion to reposition the leg before a cut; interaction of the surgical assistant with retractors; and force applied on the leg by the saw during cut execution.

Figure 2:
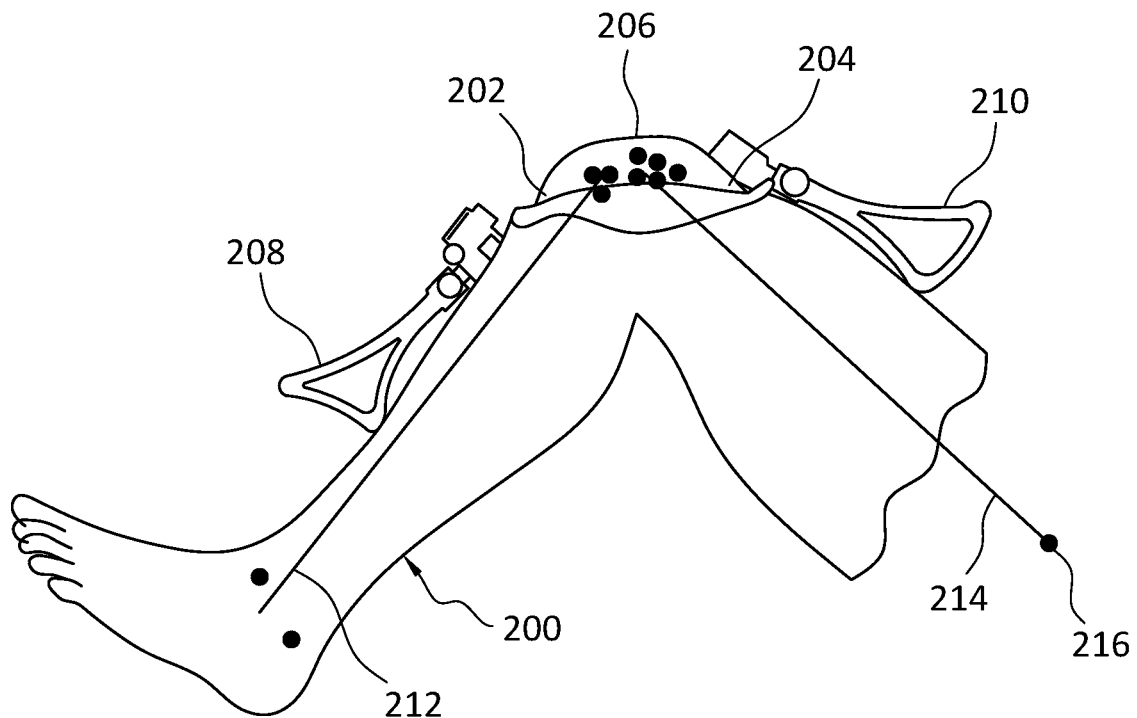
FIG. 2 illustrates a patient's leg during a knee surgery using navigation arrays.

FIG. 2 illustrates a patient's leg during a navigated knee surgery. The leg 200 is shown as positioned in an elevated bent position. The knee 206 is exposed for the surgery. A tibia navigation array 208 is attached to the tibia 202. A femur navigation array 210 is attached to the femur 204. During a typical knee replacement procedure, different kinds of anatomical landmarks are acquired intraoperatively. These landmarks can be acquired by having the surgeon place a pointer on a specific position on patient anatomy. It can also be computed thanks to specific rotation of the leg executed by the user. From the localization data acquired during those dedicated surgery steps, system 100 calculates a hip center position 216, tibia axis 212 and femur axis 214. With these parameters calculated and the bone registered to the navigation arrays 208, 210, during the rest of the surgery, system 100 can then monitor motion of the navigation arrays 208, 210 and model the motion of the bones in 3D space (correspondingly calculating the location of the tibia axis 212, femur axis 214, hip center position 216, and all additional landmarks acquired of each bone in 3D space) because system 100 assumes that the navigation arrays 208, 210 are fixed to the bones. However, if the spacing between the navigation array and the bone changes, e.g., due to being bumped, then the system 100 may calculate a location for the bone that does not correspond to the actual location of the bone.

Figure 3:
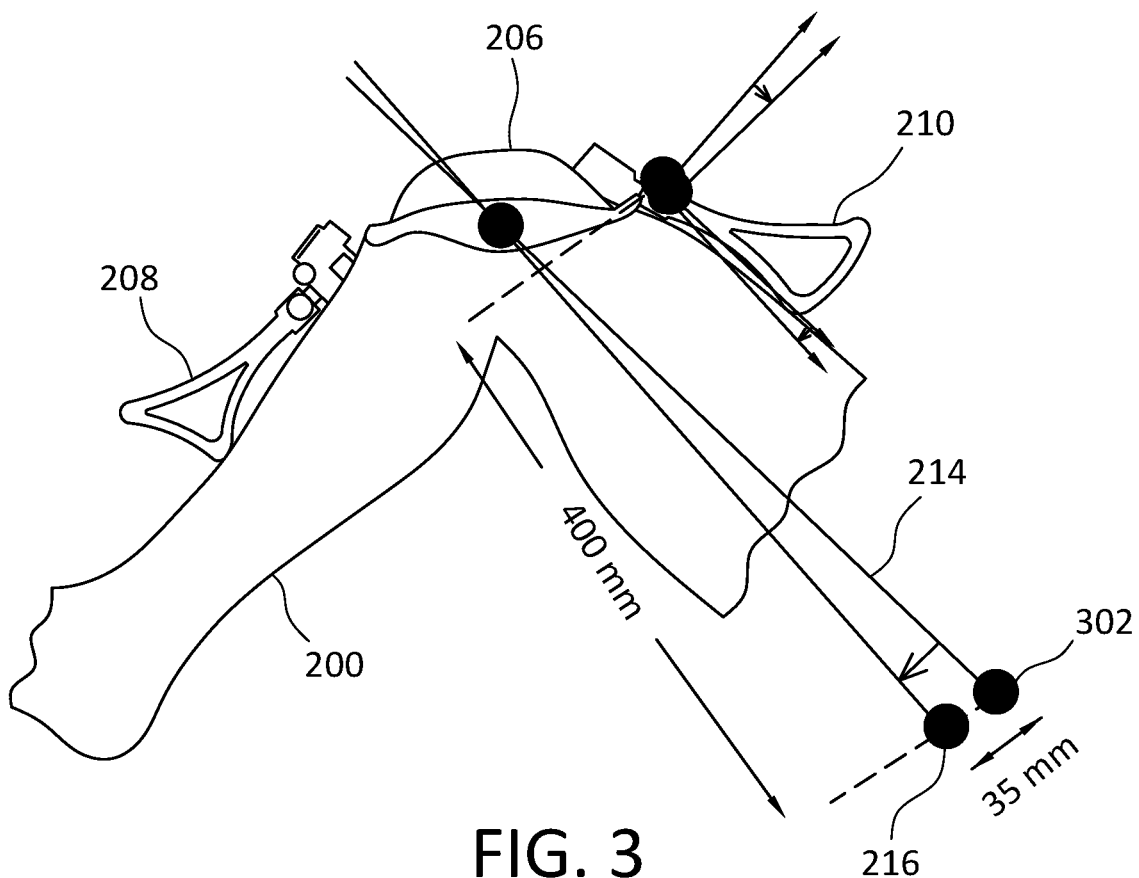
FIG. 3 illustrates the perceived motion of the hip center if the femur navigation array is rotated 5°.

The hip center position may be used to determine if the femur 204 navigation array has moved relative to the femur 204. In an alternative embodiment, a leg holder may maintain the ankle in a stable position, and the ankle position may likewise be used to determine if the tibia navigation array 208 has moved relative to the tibia 202. FIG. 3 illustrates the perceived motion of the hip center if the femur navigation array 210 is rotated 5°. Use of the hip center position 302 as the determining factor to characterize the motion detected by the tracking unit 110 has several advantages over other anatomic landmarks. For example, because the hip center is attached to the pelvis, the hip center should not move significantly during surgery (unless the patient's abdomen is moved.) Further, the hip center is located far away from the femur navigation array 210 meaning that a small motion of the array will result in a large motion of the hip center position 216. Therefore, the navigation array is placed near one end of a bone and the landmark is chosen at the other end of the bone to take advantage of this amplified movement. Various hip center motion metrics may be used that use different time spans or granularity. Frame by frame motion may be computed by determining the distance between two consecutive measures of the hip center motion. This motion may be sampled, for example, at approximately 30 Hz, but other higher or lower rates may be used. Filtered motion may be computed by comparing the first position and the last position of the hip center in a time window (e.g., 1 second, but other window sizes may be used as well). Absolute motion may be computed by comparing the current position with a reference position defined at the beginning of a step. Reference positions may be defined as an average or median of consecutive positions. Other metrics may be defined that allow for navigation array movement relative to the bone to be differentiated from other types of movement of the navigation array. Further, other landmarks may be used for other surgeries based upon the specific anatomy being used and the steps carried out during the surgery. Examples of data collected for various types of movement will now be presented. These examples will provide insights regarding how to determine if the metrics illustrate movement of the navigation array relative to the bone or other kind of array movement events.

Figure 4A:
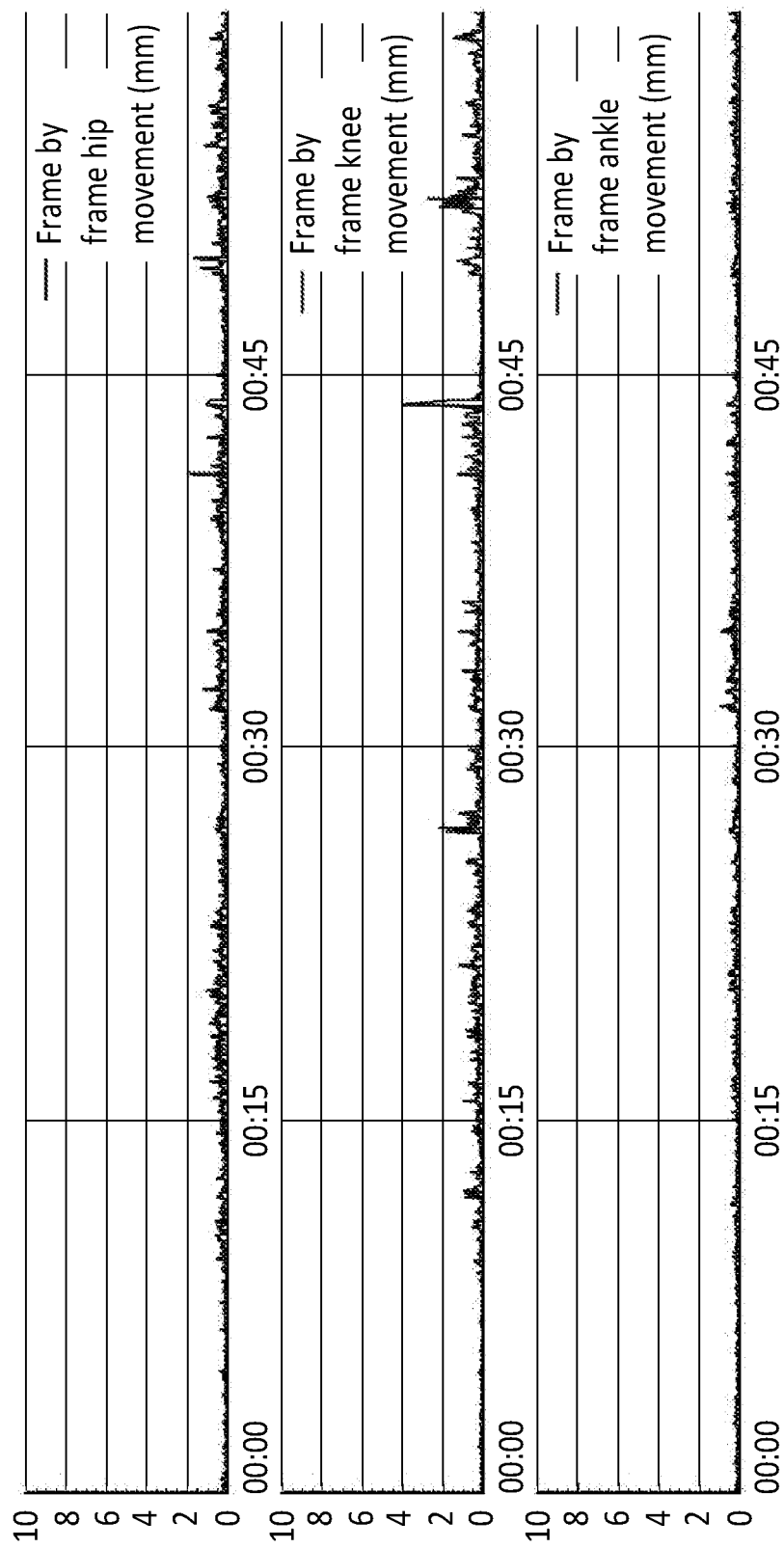
FIGS. 4A-C illustrate the motion of some anatomical landmarks during a surgical step where there is no significant motion event.
Figure 4B:
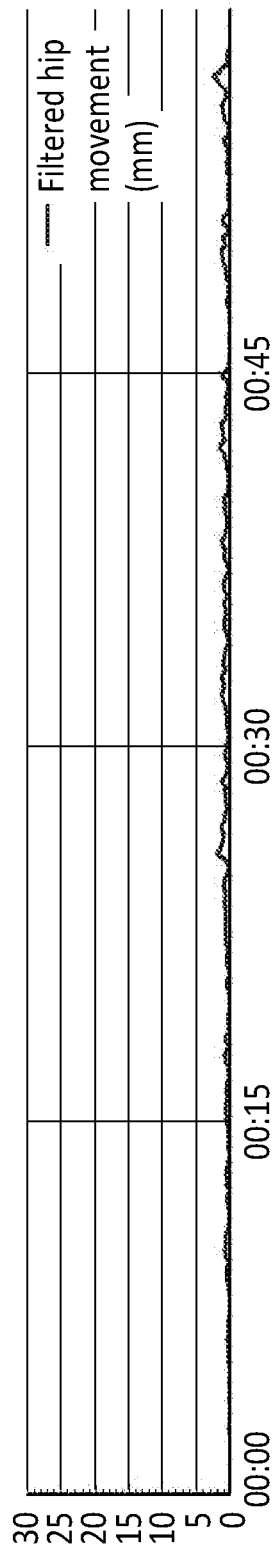
Figure 4C:
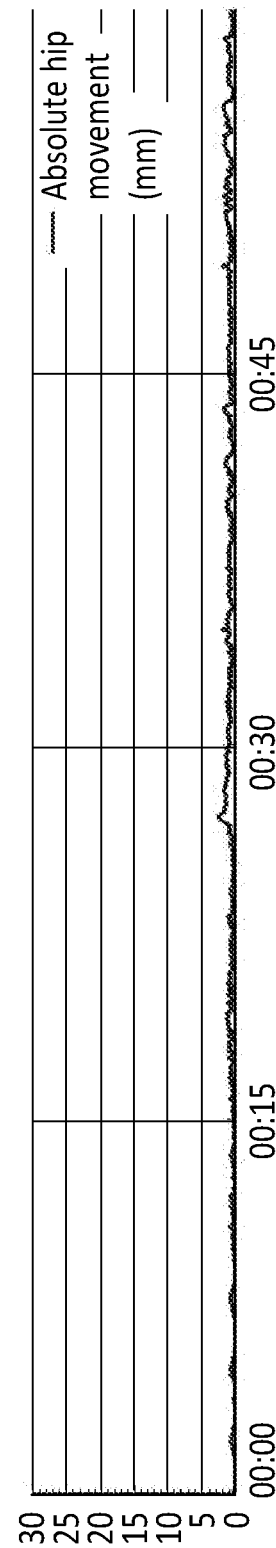

FIGS. 4A-C illustrate the motion of some anatomical landmarks during a surgical step where there is no significant motion event. The plots represent frame by frame motion for 3 specific landmarks of knee surgery: hip center, knee center ankle center. Those positions are computed from position of arrays given by the localization system. The frame represents the localization data sent at a high frequency by the localization system.

FIG. 4A illustrates three plots of sampled frame by frame motion for hip center movement (top plot), knee movement (middle plot), and ankle movement (bottom plot) in a normal surgical step where there is no significant array motion event. The vertical axis is the change in position between samples of the locations in mm of the hip center, knee, and ankle respectively. The horizontal axis is time of the measurement. In this example, the location of the hip center, knee, and ankle are each sampled at a 30 Hz rate. The difference between samples is calculated and is then plotted. FIG. 4B illustrates a plot of filtered hip center motion. This is calculated by determining reference positions of the hip center at the beginning and at the end of a time window and calculating the difference between those positions. The value of this metric is to highlight time windows where there is significant landmarks motion while filtering landmarks motion events that are brief and can be considered as not significant. The vertical axis indicates the difference, and the horizontal axis indicates the center of the observed time window. FIG. 4C illustrates a plot of the absolute hip center motion compared to a reference position defined at the beginning of the step, the first time the array is detected by the localization system. Even in a normal step where there is no significant motion event, the plots show some low amplitude movements of the different landmarks that may be due to micro-movements of the leg or noise.

Figure 5A:
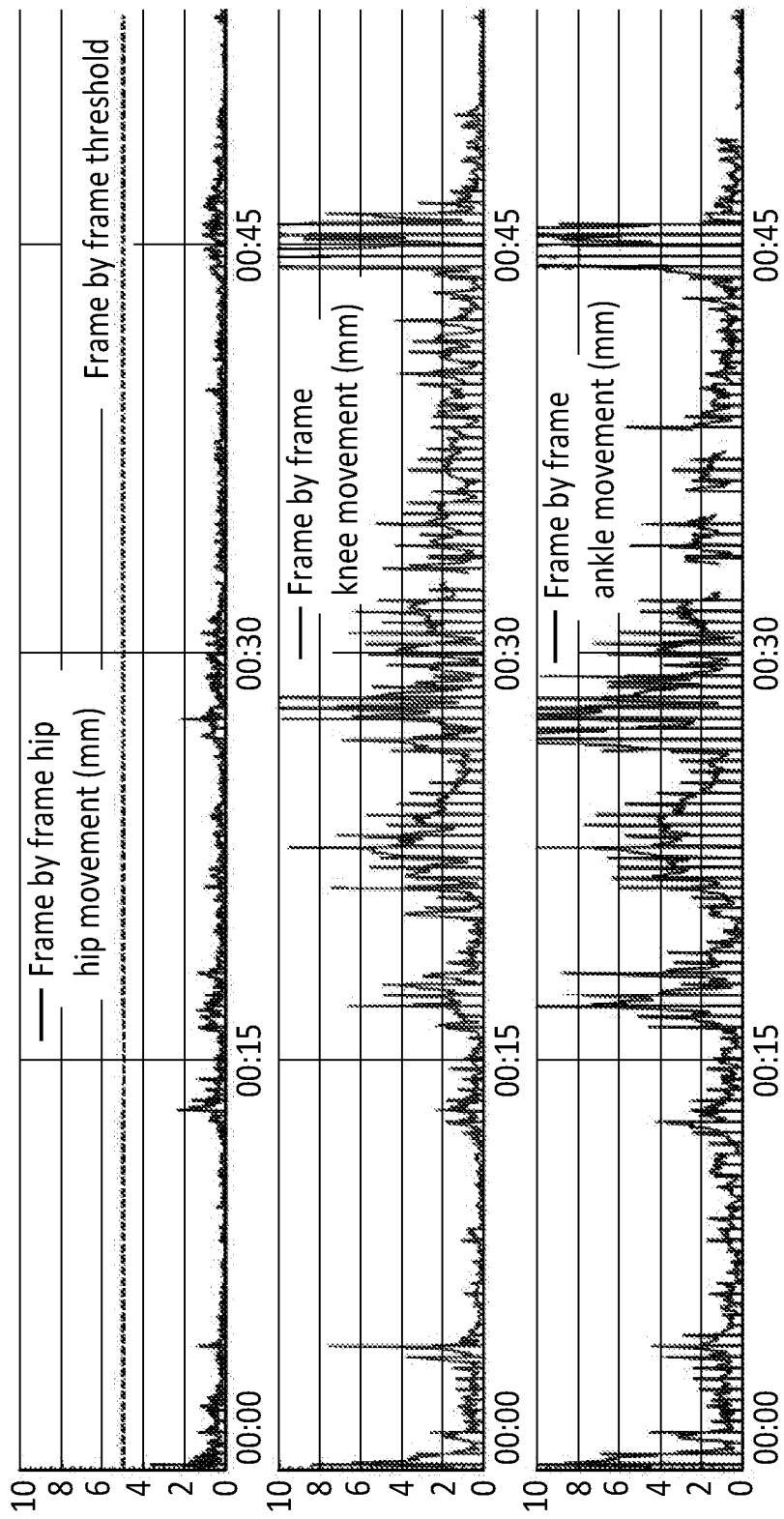

FIGS. 5A-C represents plots of landmarks motion in a surgical step where the leg moves significantly. The hip landmark plots illustrate that the hip center is a substantially fixed point that should not move above threshold values under normal surgical conditions. FIG. 5A illustrates three plots of sampled frame by frame motion for hip center movement (top plot) and knee movement (middle plot) when the knee moves. FIG. 5B illustrates a plot of filtered hip center motion. FIG. 5C illustrates a plot of the absolute hip center motion.

The plots in FIG. 5A-C illustrate that the hip center is a substantially fixed point that may be used as a landmark to detect when the navigation array moves relative to the bone. The use of a fixed landmark will help a navigation array detection algorithm to determine that the navigation array has not moved relative to the bone.

Figure 6A:
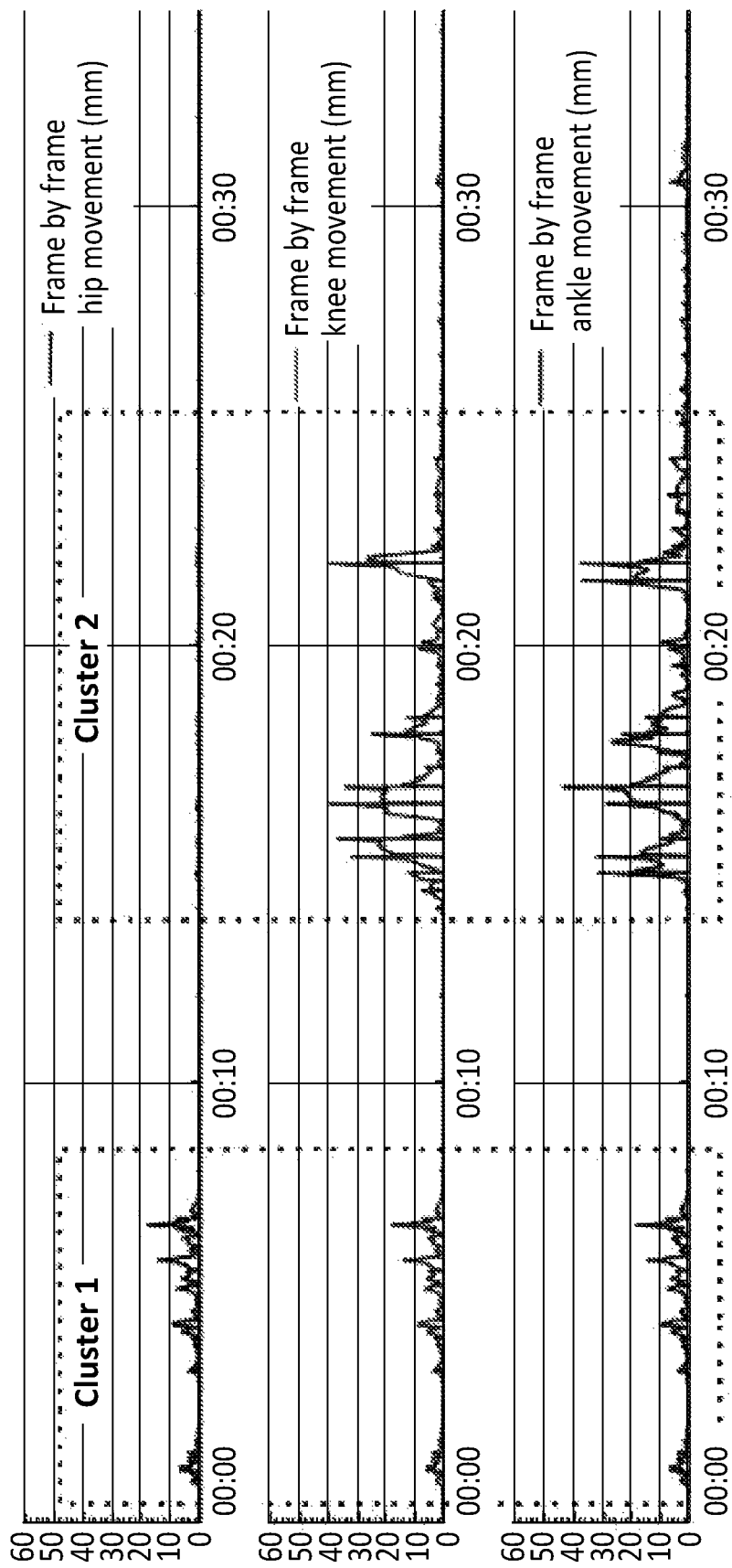

FIGS. 6A-C represent plots of landmarks motion in a surgical step where there is both camera and leg motion events. Comparison of frame-by-frame motion of the hip center with other leg landmarks in FIG. 6A shows that the hip center motion is significantly smaller Furthermore, FIGS. 6A-C show that filtered hip center motion and absolute hip center motion amplitudes are limited when the knee moves, meaning that some thresholds can be defined on the different metrics to determine what can be explained by a usual leg motion and what is a suspicious motion. As a result, the hip center will be a good landmark to measure and analyze to determine when the navigation array moves relative to the bone.

FIGS. 6A-C plot the same metrics as FIGS. 4A-C in a step where there are 2 categories of motion events in the same surgery step: one camera motion event and one leg motion event.

FIG. 6A shows the frame by frame metrics for the hip, knee and ankle center landmarks. Two clusters of motion events can be distinguished for the 3 landmarks. The first cluster shows an impact of the motion that is almost the same and simultaneous for all the observed landmarks. This is consistent with camera motion event characteristics. The second cluster shows that ankle center and knee center are similarly impacted with some slight differences, but the impact on the hip center is very low. This is consistent with leg motion characteristic. Moreover FIGS. 6B and 6C, show that cluster 1 results in a significant impact on filtered and absolute motion metrics for hip center, whereas cluster 2 does not. This confirms that the motion described by cluster 1 is a camera motion, whereas the motion described by cluster 2 is a leg motion.

Figure 7A:
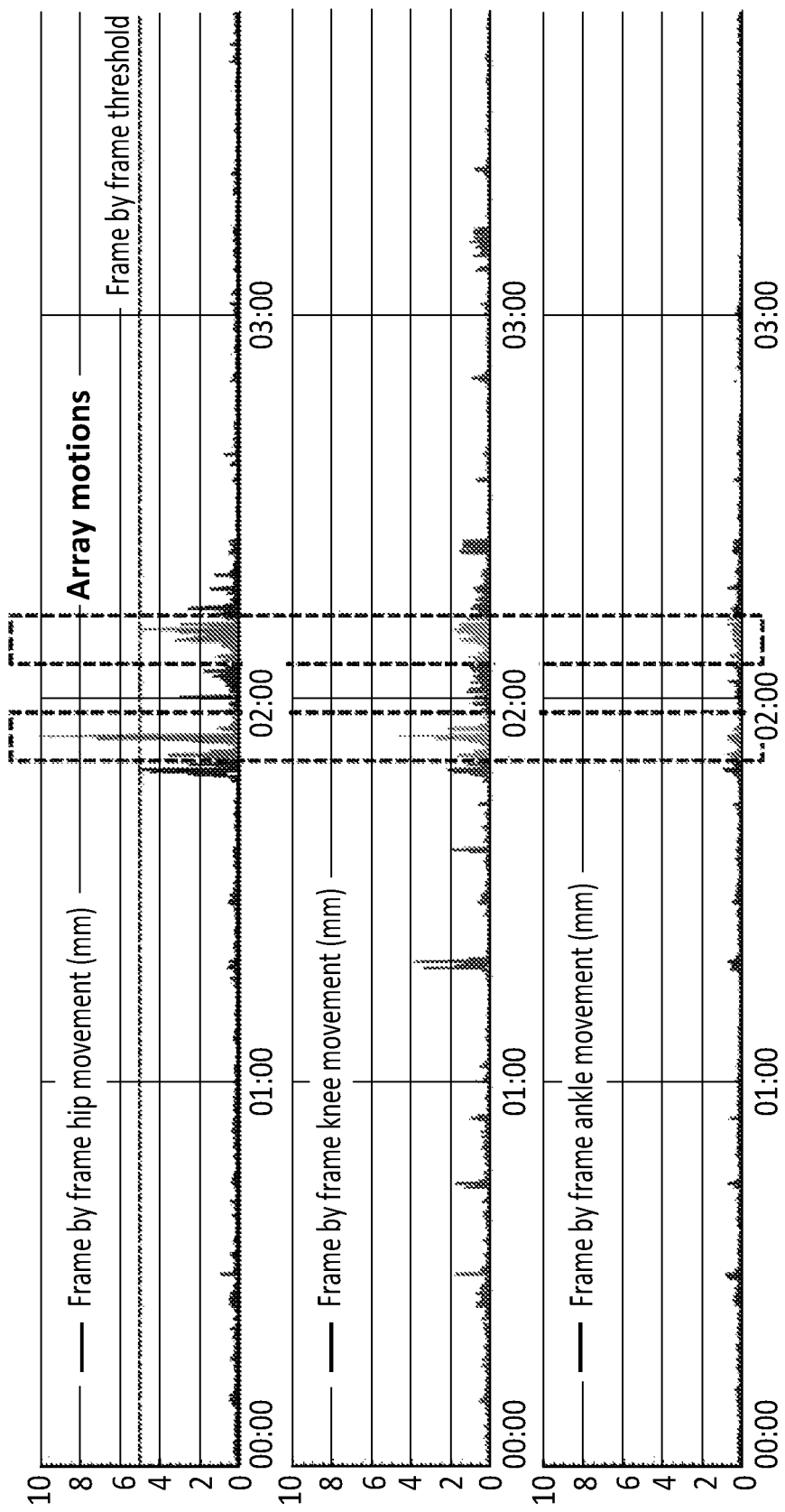

FIGS. 7A-C plot the same metrics as FIGS. 4A-C but for when the femur array moves relative to the bone. FIG. 7A illustrates the frame by frame motion for hip center movement (top plot), knee movement (middle plot), and ankle movement (bottom plot). In this case, the motion of hip center landmark has the biggest amplitude and is not synchronous with other landmarks motion. FIG. 7B illustrates the plot of filtered hip center motion. In this case, the filtered motion is above the defined threshold when the array motion event occurs. FIG. 7C illustrates the plot of the absolute hip center motion. In this case, the filtered motion is above the defined threshold when the array motion event occurs.

The frame by frame plot of the hip center in FIG. 7A illustrates a large peak at about 2:00 and a small peak at about 2:10. This leads to the two spikes in FIG. 7B at the same times. Then FIG. 7C shows two jumps in the absolute hip center movement at the same time and a resulting plateau in the plot where the hip center never returns to its initial position. These plots show a similar but reduced impact on the knee location and no impact on the ankle location. The characteristics of the motion can be compared to characteristics of other types of motion events shown in FIG. 6. The array motion results in a similar impact on hip center filtered and absolute metrics as camera motion, but the array motion does not impact other landmarks similarly as camera motion does. The array motion also has a more important impact on hip center metrics than on knee center metrics, whereas the opposite is observed for leg motion. As a result, such plots may be used to develop threshold values for the hip center movement, where hip center movement above these threshold values for one or several metrics indicates that the motion detected cannot result from a normal event during surgery and is probably due to the navigation array moving relative to the bone.

Based upon the above examples, other metrics may be explored to determine if they help differentiate navigation array movement relative to the bone. An example of other metrics would be the angle of the femur relative to the tibia in the case of knee surgery. Metrics regarding this angle may be collected and used as well to determine navigation array motion relative to the bone. Once a set of metrics have been defined, a significant number of known array motions and normal cases may be collected. This data may then be used to train a navigation array movement detector that determines threshold values to use on the various metrics in order to achieve a specified detection/false positive ratio. The navigation array movement detector may be implemented using various statistical detection methods or machine learning models. In the case of statistical detection methods, a search may be conducted for a set of thresholds for the various metrics that achieve a specified detection/false positive ratio on a set of training data that includes metric data for normal movement cases. The training data may also include data collected for situations where the navigation array moved. In the case of machine learning models a model architecture may be selected and then trained using training data until a specified detection/false positive ratio is obtained or until an optimization metric is minimized. Any type of machine learning model may be used that achieves the desired performance. Further, a few different types of machine learning model architectures may be selected and trained. Then the resulting model that has the best performance may be used as the navigation array movement detector.

In the examples above, absolute difference data was used. It is noted that each patient has a different sized anatomy. Those with a longer femur will see greater perceived movement of the hip center when the navigation array moves while those with shorter femur will see lesser movement. As a result, the data may be normalized by femur length or another appropriate bone length. Then the use of the normalized data will be less susceptible to variations in the size of the patient anatomy.

As discussed above, the navigation array motion detector may be applied to bones and landmarks other than the hip center during knee surgery, including for example, elbow surgery, ankle surgery, shoulder, etc. The reference landmark used for navigation array motion detection should be positioned on the bone as far away from the navigation array as possible, i.e., the reference landmark is near one end of the bone and the navigation array is near the other end of the bone. Further, the landmark used should be stable with no or minimal motion expected during normal surgical steps.

For example, the end of the tibia 202 at the ankle could be used to detect motion of the tibia navigation array 208 relative to the tibia 202 during knee surgery. Often the ankle may move a lot during knee surgery, so if a leg holder is used to immobilize the ankle, the navigation array motion detector may be used to detect movement of the tibia navigation array 208 relative to the tibia 202.

Figure 8:
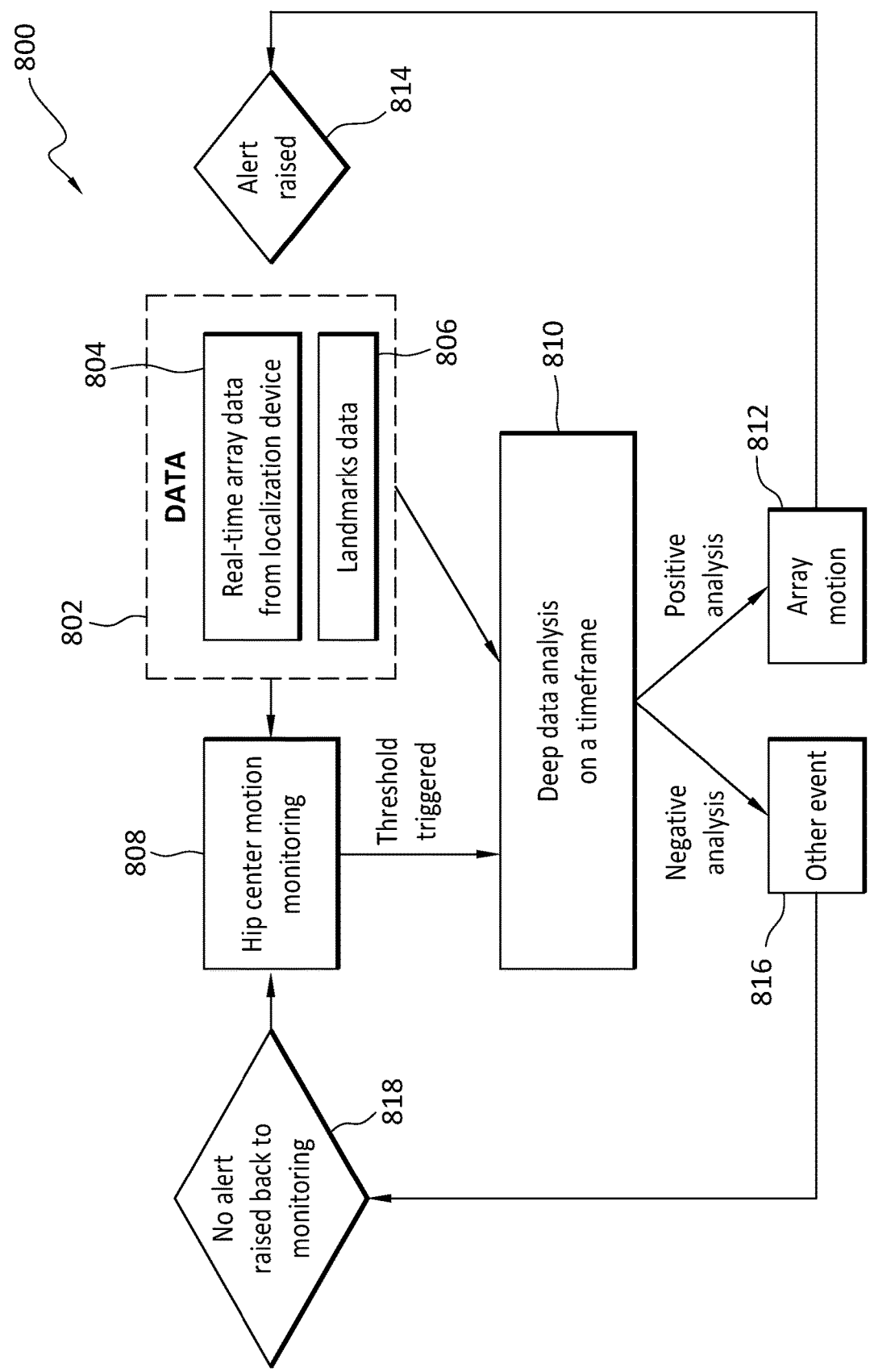
FIG. 8 illustrates a flow diagram of a high-level method for detecting the movement of a navigation array relative to a bone.

FIG. 8 illustrates a flow diagram of a high-level method for detecting the movement of a navigation array relative to a bone. The navigation array movement detection method 800 starts by monitoring and collecting landmark motion metrics 802 that that may include real-time array data from a localization device 804 and landmarks data 806. Various motion data may be measured by the tracking unit 110. This data may then be used to calculate metrics used to detect a suspicious navigation array movement that may be due to a motion of the navigation array relative to the bone. For example, the data described in FIGS. 4-7 may be calculated as described above, as well as other metrics that provide insight regarding navigation array movement. The navigation array movement detection method 800 then monitors hip center motion 808. The motion of the hip center may be compared to a threshold value as described above. This process is continuously carried out. When the motion of the hip center exceeds a threshold value, then the detection method 800 performs a deep data analysis on a timeframe 810. This analysis may be based upon the insights gained based upon the plots in FIGS. 4-7. If the deep data analysis determines that there is array motion 812, then an alert is raised 814. If the deep data analysis determines that the threshold was exceeded because of other events 816, the detection method 800 does not raise an alert and returns to monitoring 818.

Figure 9:
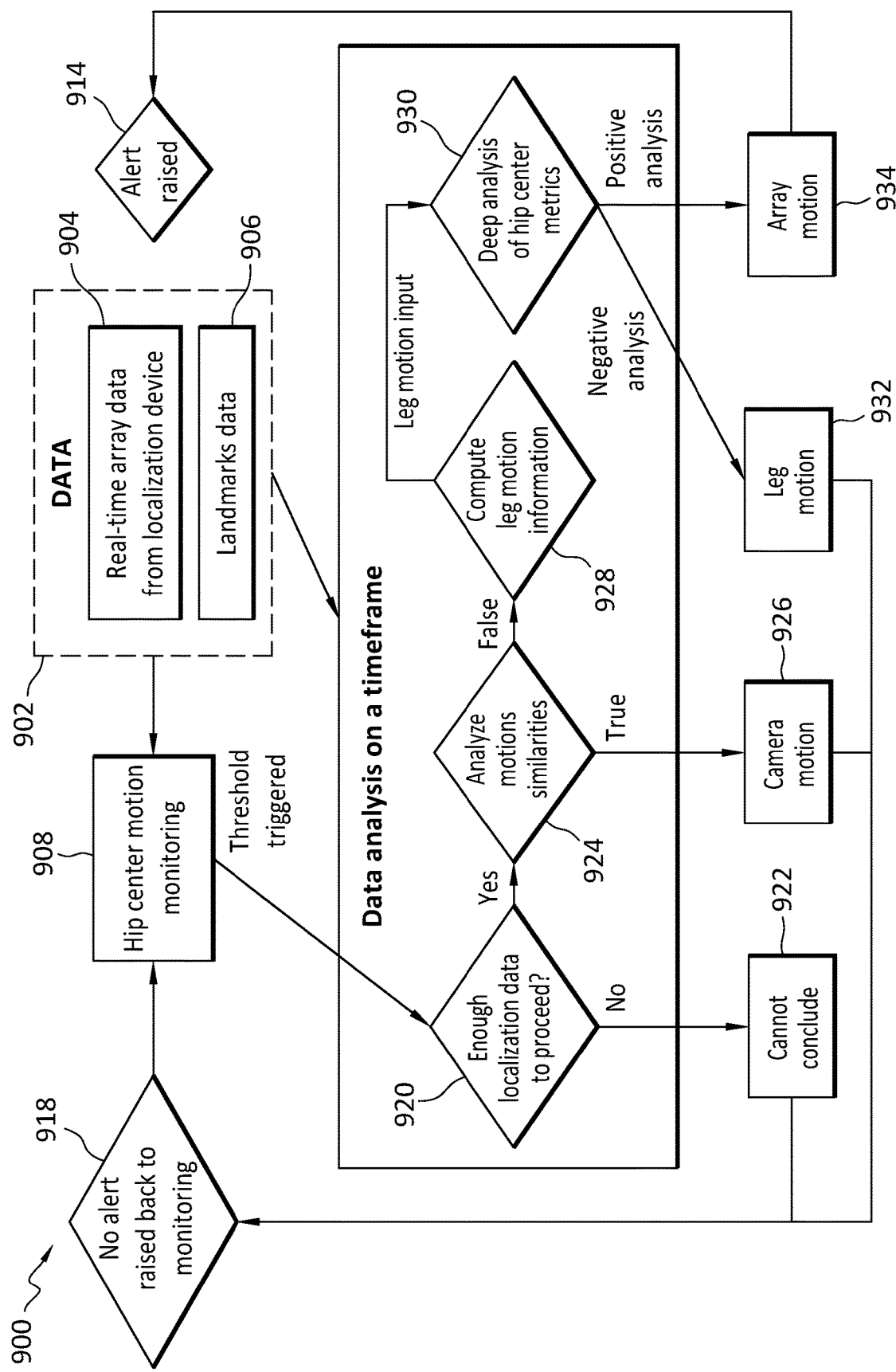
FIG. 9 illustrates another method for detecting the movement of a navigation array relative to a bone.

FIG. 9 illustrates a flow diagram of another method for detecting the movement of a navigation array relative to a bone. The navigation array movement detection method 900 starts by monitoring and collecting landmark motion metrics 902 that that may include real-time array data from a localization device 904 and landmarks data 906. Various motion data may be measured by the tracking unit 110. This data may then be used to calculate metrics used to detect suspicious navigation array movement that may be due to a motion of the navigation array relative to the bone. For example, the data described in FIGS. 4-7 may be calculated as described above, as well as other metrics that provide insight regarding navigation array movement. The navigation array movement detection method 900 then monitors hip center motion 908. The motion of the hip center may be compared to a threshold value as described above. This process is continuously carried out. When the motion of the hip center exceeds a threshold value, then the detection method 900 determines if there is enough localization data to proceed 920. If not, then the detection method 900 cannot come to a conclusion 922 and does not raise an alert and returns to monitoring 918. If there is enough localization data to proceed, the detection method 900 analyzes the similarities of the motions 924. The definition of similarities in this context relies on an underlying camera motion model that could include different kind of transformation including translation and rotation. Landmarks motions are considered as similar if they can result from the same transformation among the possibilities described in the model. This may be accomplished using various methods such as thresholding, correlation, etc. If the various motions of visible landmarks or arrays respects the similarity criteria, then this indicates camera motion 926 and again no alert is raised and monitoring resumes 918. If the motions are not similar, then leg motion information may be computed 928. Then the detection method 900 may perform deep analysis of hip center metrics 930 using the leg motion input. If the deep analysis of hip center metrics determines that the hip motion is due to leg motion 932, then no alert is raised and monitoring is resumed 918. If the deep analysis of leg hip center metrics determines that there is array motion 934, then an alert indicating array motion is raised 914.

The aim of the steps 928 and 930 is to refine the analysis depending on the leg motion amplitude that may have happened during the analyzed timeframe. Step 928 determines metrics that help characterizing the leg motion. It can include, for example, the knee center motion, or the difference in leg angle (angle between tibia and femur axes) in the timeframe. Step 930 utilizes leg motion metrics from step 928 with hip center metrics to determine if the hip center metrics can be explained only by the leg motion, or if an array motion happened. This can be achieved for example by an adaptative thresholding. If the absolute landmark motion metric is less than the threshold associated to current leg motion, then then leg motion is indicated 932. In the opposite case, the navigation array movement detection method 900 raises an array motion warning 934 and 914.

In an alternative embodiment, steps 920, 924, 928, and 930 may be replaced by a machine learning model. The machine learning model may take as inputs motion metrics, such as for example, hip center motion, knee center motion, and absolute hip center motion. Other metrics that show the ability to differentiate between the various movement scenarios that might occur during the surgery may also be used. The output of the machine leaning model would be an indication of whether the navigation array has moved relative to the bone. This machine learning model would be produced by selecting a machine learning model architecture and then using training data to train the model where the training data covers a wide range of movements that occur during surgery. The model may be trained using standard training and optimization methods. Also, various machine learning model architectures may be selected and trained as well. Then the best performing model may be used to detect when the navigation array moves relative to the bone.

Figure 10:
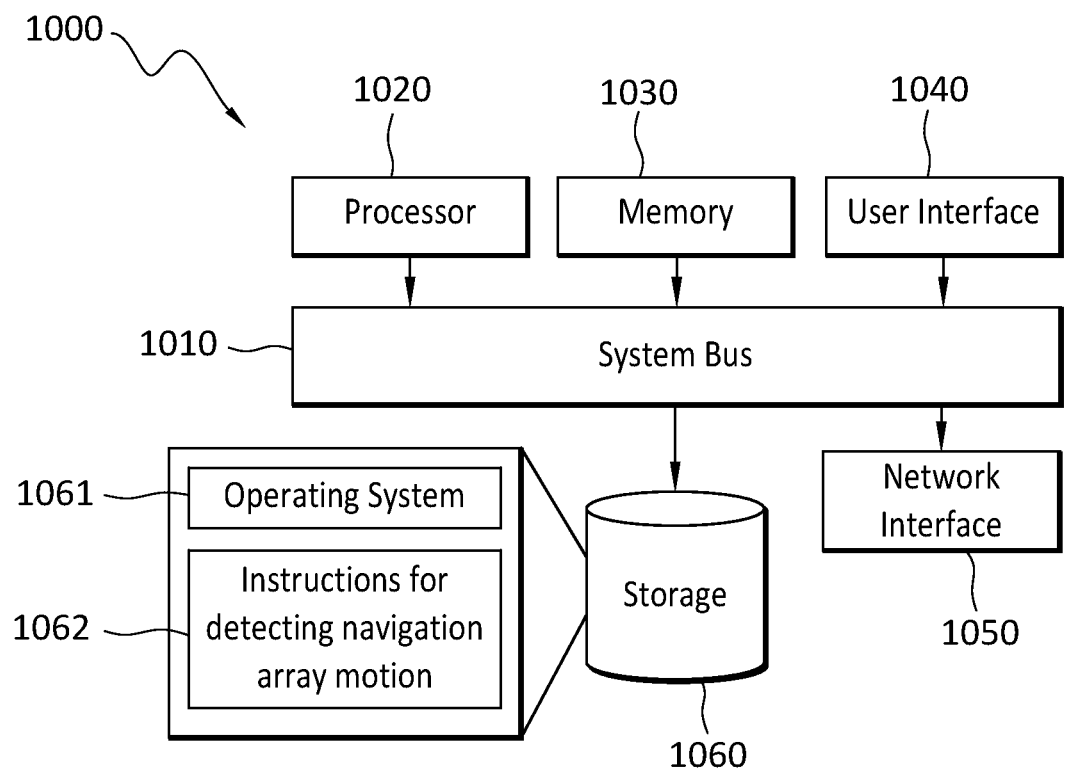
FIG. 10 illustrates an exemplary hardware diagram for implementing a navigation array movement detector.

FIG. 10 illustrates an exemplary hardware diagram 1000 for implementing a navigation array movement detector. The exemplary hardware 1000 may correspond to the tracking unit 110, external device 108, a connected processor or computer system, or some other processor available in the computer-assisted surgical system 100. As shown, the device 1000 includes a processor 1020, memory 1030, user interface 1040, network interface 1050, and storage 1060 interconnected via one or more system buses 1010. It will be understood that FIG. 10 constitutes, in some respects, an abstraction and that the actual organization of the components of the device 1000 may be more complex than illustrated.

The processor 1020 may be any hardware device capable of executing instructions stored in memory 1030 or storage 1060 or otherwise processing data. As such, the processor may include a microprocessor, microcontroller, graphics processing unit (GPU), neural network processor, field programmable gate array (FPGA), application-specific integrated circuit (ASIC), or other similar devices.

The memory 1030 may include various memories such as, for example L1, L2, or L3 cache or system memory. As such, the memory 1030 may include static random-access memory (SRAM), dynamic RAM (DRAM), flash memory, read only memory (ROM), or other similar memory devices.

The user interface 1040 may include one or more devices for enabling communication with a user. The user interface 1040 may be part of external device 108. For example, the user interface 1040 may include a display, a touch interface, a mouse, and/or a keyboard for receiving user commands. In some embodiments, the user interface 1040 may include a command line interface or graphical user interface that may be presented to a remote terminal via the network interface 1050.

The network interface 1050 may include one or more devices for enabling communication with other hardware devices. For example, the network interface 1050 may include a network interface card (NIC) configured to communicate according to the Ethernet protocol or other communications protocols, including wireless protocols. Additionally, the network interface 1050 may implement a TCP/IP stack for communication according to the TCP/IP protocols. Various alternative or additional hardware or configurations for the network interface 1050 will be apparent.

The storage 1060 may include one or more machine-readable storage media such as read-only memory (ROM), random-access memory (RAM), magnetic disk storage media, optical storage media, flash-memory devices, or similar storage media. In various embodiments, the storage 1060 may store instructions for execution by the processor 1020 or data upon with the processor 1020 may operate. For example, the storage 1060 may store a base operating system 1061 for controlling various basic operations of the hardware 1000. The storage 1062 may store instructions for implementing the navigation array detector as described herein.

It will be apparent that various information described as stored in the storage 1060 may be additionally or alternatively stored in the memory 1030. In this respect, the memory 1030 may also be considered to constitute a "storage device" and the storage 1060 may be considered a "memory." Various other arrangements will be apparent. Further, the memory 1030 and storage 1060 may both be considered to be "non-transitory machine-readable media." As used herein, the term "non-transitory" will be understood to exclude transitory signals but to include all forms of storage, including both volatile and non-volatile memories.

The system bus 1010 allows communication between the processor 1020, memory 1030, user interface 1040, storage 1060, and network interface 1050.

While the host device 1000 is shown as including one of each described component, the various components may be duplicated in various embodiments. For example, the processor 1020 may include multiple microprocessors that are configured to independently execute the methods described herein or are configured to perform steps or subroutines of the methods described herein such that the multiple processors cooperate to achieve the functionality described herein. Further, where the device 1000 is implemented in a cloud computing system, the various hardware components may belong to separate physical systems. For example, the processor 1020 may include a first processor in a first server and a second processor in a second server.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A method of detecting movement of a first navigation array relative to a bone during computer-assisted surgery, comprising:
   monitoring a location of a landmark on the bone using the first navigation array, wherein the landmark is at a first end of the bone and the first navigation array is adjacent to a second end of the bone;
   determining that the location of the landmark has moved a distance greater than a threshold value;
   indicating suspicious activity when the distance is greater than the threshold value;
   monitoring the location of a second navigation array;
   analyzing a similarity of a motion of the second navigation array and the landmark when suspicious activity is indicated; and
   determining that the suspicious activity is camera motion when the motion of the second navigation array and the landmark are similar.

2. The method of claim 1, wherein analyzing the similarity of the motion of the second navigation array and the landmark includes:
   monitoring a frame-to-frame movement of the landmark and the second navigation array; and
   comparing the frame-to-frame movement of the landmark to the frame-to-frame movement of the second navigation array.

3. The method of claim 1, further comprising:
   computing bone motion information;
   computing landmark metrics based upon the computed bone motion information; and
   analyzing landmark metrics to determine whether bone motion information indicates that the suspicious activity is array motion.

4. The method of claim 2, further comprising:
   analyzing landmark metrics based upon bone motion information to determine whether bone motion information indicates that the suspicious activity is bone motion.

5. The method of claim 1, wherein the computer-assisted surgery is a knee surgery and the landmark is a hip center.

6. The method of claim 1, wherein the landmark is at a location that moves less than a threshold value during the computer-assisted surgery.

7. A method of detecting movement of a first navigation array relative to a bone during computer-assisted surgery, comprising:
   monitoring a location of a landmark on the bone using the first navigation array, wherein the landmark is at a first end of the bone and the first navigation array is adjacent to a second end of the bone;
   determining that the location of the landmark has moved a distance greater than a threshold value;
   indicating suspicious activity when the distance is greater than the threshold value;
   monitoring the location of a second navigation array; and
   analyzing, using a machine learning model, a similarity of a motion of the second navigation array and the landmark and determining that the suspicious activity is camera motion when the motion of the second navigation array and the landmark are similar.

8. The method of claim 7, further comprising:
   computing bone motion information;
   computing landmark metrics based upon the computed bone motion information; and
   analyzing, using a machine learning model, landmark metrics to determine whether bone motion information indicates that the suspicious activity is array motion or is bone motion.

9. A method of detecting movement of a first navigation array relative to a bone during computer-assisted surgery, comprising:
   registering a location of a landmark on the bone relative to the first navigation array;
   monitoring the location of the landmark on the bone by modeling the motion of the bone using the first navigation array, wherein the landmark is at a first end of the bone and the first navigation array is adjacent to a second end of the bone;
   determining that the location of the landmark has moved a distance greater than a threshold value; and
   indicating suspicious activity when the distance is greater than the threshold value;
   registering a location of a landmark on the bone relative to a second navigation array;
   monitoring the location of a second navigation array;
   analyzing a similarity of a motion of the second navigation array and the landmark when suspicious activity is indicated; and
   determining that the suspicious activity is camera motion when the motion of the second navigation array and the landmark are similar.

10. The method of claim 9, wherein analyzing the similarity of the motion of the second navigation array and the landmark includes:
    monitoring a frame-to-frame movement of the landmark and the second navigation array; and
    comparing the frame-to-frame movement of the landmark to the frame-to-frame movement of the second navigation array.

11. The method of claim 9, further comprising:
computing bone motion information;
computing landmark metrics based upon the computed bone motion information; and
analyzing landmark metrics to determine whether bone motion information indicates that the suspicious activity is array motion.

12. The method of claim 10, further comprising:
analyzing landmark metrics based upon bone motion information to determine whether bone motion information indicates that the suspicious activity is bone motion.

13. The method of claim 9, wherein the computer-assisted surgery is a knee surgery and the landmark is a hip center.

14. The method of claim 9, wherein the landmark is at a location that moves less than a threshold value during the computer-assisted surgery.

15. A method of detecting movement of a first navigation array relative to a bone during computer-assisted surgery, comprising:
registering a location of a landmark on the bone relative to the first navigation array;
monitoring the location of the landmark on the bone by modeling the motion of the bone using the first navigation array, wherein the landmark is at a first end of the bone and the first navigation array is adjacent to a second end of the bone;
determining that the location of the landmark has moved a distance greater than a threshold value; and
indicating suspicious activity when the distance is greater than the threshold value;
registering a location of a landmark on the bone relative to a second navigation array;
monitoring the location of a second navigation array; and
analyzing, using a machine learning model, a similarity of a motion of the second navigation array and the landmark and determining that the suspicious activity is camera motion when the motion of the second navigation array and the landmark are similar.

16. The method of claim 15, further comprising:
computing bone motion information;
computing landmark metrics based upon the computed bone motion information; and
analyzing, using a machine learning model, landmark metrics to determine whether bone motion information indicates that the suspicious activity is array motion of the second navigation array or is bone motion.

* * * * *